United States Patent [19]

Kauffman

[11] Patent Number: 4,744,870
[45] Date of Patent: May 17, 1988

[54] METHOD FOR EVALUATING THE REMAINING USEFUL LIFE OF A LUBRICANT

[75] Inventor: Robert E. Kauffman, Kettering, Ohio

[73] Assignee: University of Dayton, Dayton, Ohio

[21] Appl. No.: 945,755

[22] Filed: Dec. 23, 1986

[51] Int. Cl.$^4$ ............................................. G01N 27/48
[52] U.S. Cl. ....................................... 204/1 T; 436/60
[58] Field of Search ................... 436/60, 61; 204/1 T, 204/1 K

[56] References Cited

U.S. PATENT DOCUMENTS

| | | | |
|---|---|---|---|
| 3,003,350 | 10/1961 | Stewart | 73/64 |
| 3,182,255 | 5/1965 | Hopkins et al. | 324/61 |
| 3,526,127 | 9/1970 | Sarkis | 73/64 |
| 4,029,554 | 6/1977 | Ellison | 204/1 T |
| 4,082,511 | 4/1978 | Bedford | 73/64 X |
| 4,317,705 | 3/1982 | Hamada et al. | 204/1 T |

OTHER PUBLICATIONS

Donald T. Sawyer et al., "Experimental Electro-Chemistry For Chemists", pp. 329–394, (1974).

Primary Examiner—Kaplan G. L.
Attorney, Agent, or Firm—Biebel, French & Nauman

[57] ABSTRACT

A method is disclosed for measuring the remaining useful life of an ester-based lubricant containing at least one antioxidant species. A lubricant sample is mixed with a solvent, an organic base and an electrolyte to produce an analysis sample. The analysis sample is placed into an electrolytic cell and subjected to a cyclic voltammetric analysis, whereby a varying electric current is produced within the cell. The current during the cyclic voltammetric analysis is measured and recorded. Remaining useful life for the lubricant is then determined from the average maximum reduction current wave height produced.

27 Claims, 3 Drawing Sheets

METHOD FOR EVALUATING THE REMAINING USEFUL LIFE OF A LUBRICANT

The United States government has rights in this invention, pursuant to Contract No. F33615-83-C-2317 awarded by the Department of the Air Force.

BACKGROUND OF THE INVENTION

The present invention relates generally to oils used as lubricants and, more specifically, to a method for evaluating such lubricants during use to determine their remaining useful life. The method is particularly adapted for use with ester-based oils.

It is common to lubricate and cool the components of operating equipment by wetting them with an oil lubricant. Such a lubricant experiences various environmental stresses as it carries out such functions that cause its basestock to undergo thermal-oxidative degradation. For this reason, various antioxidants are added to the lubricant to protect its lubricating characteristics. So long as the antioxidant system remains intact, the oxidative degradation of the basestock, and hence the changes in the lubricant's properties, are minimal.

Antioxidant species within a lubricating oil are gradually depleted with equipment operating time. Eventually, the antioxidants become ineffective, which allows large changes to occur in the physical properties of the lubricant's basestock. At such point, the lubricant is no longer capable of protecting the equipment and its useful life ends, resulting in excessive component wear and eventual failure of the equipment.

Since it is undesirable to continue to use a lubricant beyond the end of its useful life, scheduled lubricant changes have been devised for various types of operating equipment. The length of equipment operating time between scheduled changes is selected quite conservatively to ensure that dysfunctional lubricant is not permitted to remain within the equipment. However, this results in lubricants with remaining useful life being discarded.

It can therefore be seen that the ability to predict the remaining useful life of a lubricant would eliminate the need to perform lubricant changes on the basis of a fixed schedule. This would permit longer use of a lubricant, thereby providing savings in material and labor costs. Further, abnormal depletion rates for antioxidants within a lubricant sample can indicate severe wear problems prior to equipment failure.

Various thermal-oxidative and chemical-oxidative stressing techniques having the capability to evaluate remaining useful life are known. However, such techniques are unsuitable for routine use. Thermal-oxidative stressing techniques require the use of high temperatures and pressures and long analysis times in the order of 30 minutes. Chemical-oxidative stressing techniques are difficult in operation, require unstable reagents, and also require long analysis times in the order of 120 minutes.

One type of lubricant in common use is ester-based oils. Such oils are often used in gas turbine engines such as are typically found in aircraft. Ground turbine engines are utilized in power generation equipment. It would be advantageous to reduce the need for lubricant changes in such engines by evaluating the lubricant to determine its particular useful lifetime.

What is needed, therefore, is a method for evaluating the remaining useful life of a lubricant which does not require the use of high temperature and pressure or unstable reagents. The method should be specifically adapted for use with an ester-based oil lubricant. Such a technique should be rapid, i.e., analysis times of less than a minute, as well as easy to operate and capable of being performed with inexpensive equipment.

SUMMARY OF THE INVENTION

The present invention provides a method for measuring the remaining useful life of a lubricant containing at least one antioxidant species, which is specifically adapted to the evaluation of ester-based lubricating oils typically used in gas turbine engines.

The method includes obtaining a lubricant sample, and mixing such sample with an organic base and a solvent to produce an analysis sample. An electrical potential of a first value is applied to the analysis sample to produce an electrical current therethrough. The potential is varied cyclically from the first value to a second value, producing an oxidation reaction of the antioxidant species, and then back to the first value, producing a reduction reaction of the oxidized product. Current produced in the cell is measured and recorded during at least the reduction reaction. These steps of cyclically varying potential and recording measured current essentially constitute a cyclic voltammetric evaluation of the analysis sample.

The organic base may preferably be pyridazine or, alternatively, pyridine or dipyridyl. The ratio by weight of the organic base to the electrolyte and the solvent within the analysis sample may be within the range of 1:300 to 1:30,000, preferably 1:3000.

The ratio by volume of the lubricant to the organic base, electrolyte and solvent within the analysis sample may be within the range of 1:5 to 1:500, preferably 1:50.

The solvent may be acetone, and the electrolyte may be lithium perchlorate ($LiClO_4$).

The first and second potential values may be within the range of $+1.5$ V and $-1.5$ V, with the preferred first and second potential values being, respectively, 0.0 V and $+1.0$ V. The potential is preferably varied at a rate witnin the range of 0.2 V/sec to 30.0 V/sec, with 5.0 V/sec being most preferred.

The maximum current produced during said reduction reaction is determined, and used to evaluate the remaining useful life for the lubricant.

Preferably, the varying of the potential from the first value to the second value and back to the first value is repeated for a plurality of times. The current is continuously measured and recorded during at least the reduction reactions produced during the varying of potential. More preferably, the cyclic varying of potential is performed ten times. In such a case, the maximum current produced during each of the sixth through tenth of the reduction reactions is determined, from which an average maximum current value is calculated.

Accordingly, it is an object of the present invention to provide a method of evaluating the remaining useful life of a lubricant; to provide a method which is specifically usable in evaluating ester-based lubricating oils; to provide such a method which does not require the use of high temperatures and pressures or unstable reagents; to provide such a method which is rapidly performed, with analysis times of less than a minute; to provide such a technique which is easy to operate and can be performed with inexpensive equipment; and to provide such a technique which requires minimal sample preparation and can be used with small sample sizes.

Other objects and advantages of the present invention will be apparent from the following description, the accompanying drawings, and the appended claims.

DETAILED DESCRIPTION OF THE PREFERRED EMBODIMENT

The method for evaluating the remaining useful life of an ester-based oil lubricant in accordance with the present invention is based generally upon cyclic voltammetric analysis of the lubricant sample. In general, voltammetric techniques are electroanalytical methods wherein a sample to be analyzed is mixed with an electrolyte and a solvent, and placed within an electrolytic cell. Data is obtained by measuring the current passing through the cell as a function of the potential applied, and test results are based upon current, voltage and time relationships at the cell electrodes.

The cell consists of a fluid container into which is mounted a small, easily polarized microelectrode, and a large non-polarizable reference electrode. The reference electrode should be massive relative to the microelectrode so that its behavior remains essentially constant with the passage of small current; that is, it remains unpolarized during the analysis. Additional electrodes, auxiliary electrodes, can be added to the electrode system to eliminate the effects of resistive drop for high resistance solutions.

Figure 1:
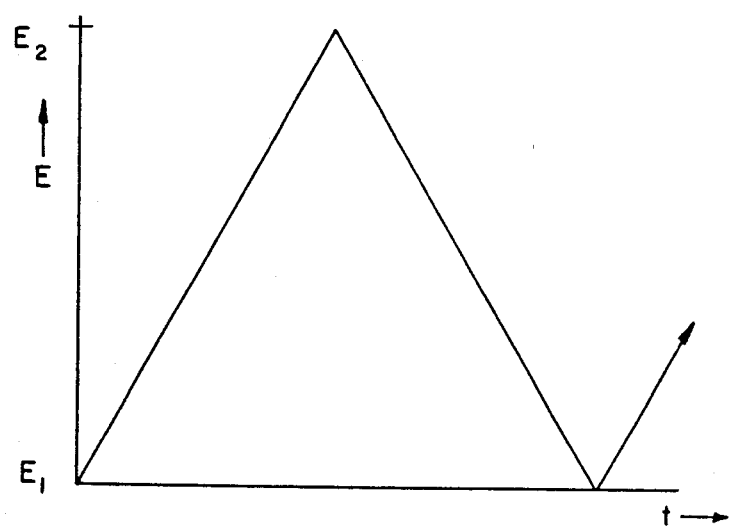
FIG. 1 is a plot illustrating potential applied to a lubricant sample as a function of time in practicing the method for evaluating remaining useful life of a lubricant in accordance with the present invention.

In performing a voltammetric analysis, the potential across the electrodes is varied linearly with time, and the resulting current is recorded as a function of the potential. A variation on this technique, known as cyclic voltammetric analysis, uses a potential variation as shown in FIG. 1. Initially, potential applied to the electrodes is of a first value $E_1$ and is linearly increased over time to the second value $E_2$. The potential is next reduced at the same rate until the potential again returns to $E_1$, producing a triangular waveform. The cycle may then be repeated.

The present invention is based upon subjecting a sample of ester-based lubricant to cyclic voltammetric analysis. As the increasing voltage is applied to the sample, the antioxidant species within the lubricant are caused to electrochemically oxidize. During voltage reduction, the oxidized species are subsequently electrochemically reduced. The data recorded during these oxidation and reduction reactions can then be used to determine the remaining useful life of the lubricant specimen.

Figure 2:
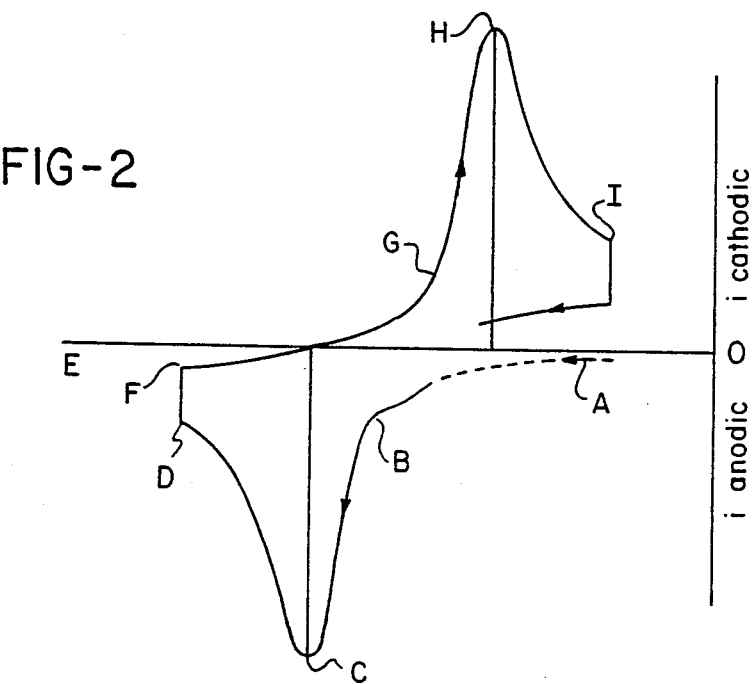
FIG. 2 is a plot illustrating current produced in the sample as a function of potential applied.

A typical current-potential curve produced during the practice of the present invention can be seen by reference to FIG. 2. Initially, as shown at point A, the applied potential produces an electrochemical reaction having a rate so slow that virtually no current flows through the cell. As the voltage is increased, shown at point B, the electro-active species, i.e., the antioxidant species in the lubricant, begin to oxidize at the microelectrode's surface, producing an anodic rise in the current. As the potential is further increased, the decrease in the electro-active species concentration at the electrode surface and the exponential increase of the oxidation rate lead to a maximum in the current-potential curve shown at point C. The current then decreases to the diffusion-limited anodic current value at point D. The peak so produced is referred to as the oxidation wave.

The direction of applied voltage is then reversed, point F, and becomes more cathodic with time. When the voltage becomes sufficiently cathodic, the oxidized species at the surface of the microelectrode begin to reduce, producing the cathodic rise in the current shown at point G. Again, a maximum current is obtained at point H, and the current decreases with decreasing potential until the cycle is completed or a new cycle is initiated at point I. This produced peak is referred to as the reduction wave.

It has been found that the height of the oxidation wave (see point C in FIG. 2) and the reduction wave (see point H in FIG. 2) can be used in evaluating the remaining useful life of an ester-based lubricant. However, performing the analysis on the lubricant alone (in solution with an electrolyte and a solvent) produces accuracies for the remaining useful life evaluations which are formula dependent.

To avoid this problem, it has been discovered that performing the cyclic voltammetric analysis of the lubricant in the presence of an organic base causes a reduction wave to be produced which is formula independent. The oxidation wave is not affected by the presence of an organic base. Numerous organic bases can be successfully used in the lubricant evaluation technique disclosed herein, but pyridazine is most preferred. Pyridine and dipyridyl are also preferred.

The preferred solvent for use in the evaluation technique is acetone, but any solvent capable of dissolving the required electrolyte and lubricant sample can be used. The preferred electrolyte for use in the technique is lithium perchlorate ($LiClO_4$), although any soluble electrolyte can be used. The appropriate amount of electrolyte is added to the solvent to produce a solution suitable for cyclic voltammetric analysis. Solutions containing 50 to 100 millimoles of lithium perchlorate per liter of acetone are preferred.

The organic base is added to the electrolyte solution. The ratio of organic base to electrolyte solution is dependent upon the particular organic base used. In the case of pyridazine, the electrolyte/organic base solution ratio, by weight, is 1:300 to 1:30,000, with 1:3000 preferred.

In one specific example, an electrolyte solution was prepared by dissolving 2.7 g of $LiClO_4$ and 160 $\mu$l of pyridazine in 500 ml of acetone.

Finally, the used lubricant sample is added to the electrolyte/organic base solution in the ratio, by volume, of 1:5 to 1:500, with 1:50 preferred. The solution is shaken by hand and then analyzed.

In the specific example noted above, a 50 $\mu$l sample of used ester-oil lubricant was dissolved in 3 ml of the electrolyte solution previously described.

In the electrolytic cell, a Ag/AgCl reference electrode is preferred. Also preferred is a glassy carbon working electrode and a platinum wire auxiliary electrode. Of course, electrodes formed from other materials are also usable.

To improve the accuracy of the evaluation results, it is preferred that ten consecutive cyclic scans be performed on each sample while recording the produced reduction waves. The average reduction wave height for the sixth through tenth scans is then used as the evaluation data.

In carrying out the cyclic voltammetric analysis, potential is varied between +1.5 and −1.5 volts, with variation between 0.0 to +1.0 volts being preferred. The voltage scan rate is preferably within the range of 0.2 V/sec. to 30.0 V/sec, with 5.0 V/sec being most preferred. Ten cyclic scans of the sample within the preferred potential range therefore requires an analysis time of four seconds.

Figure 3:
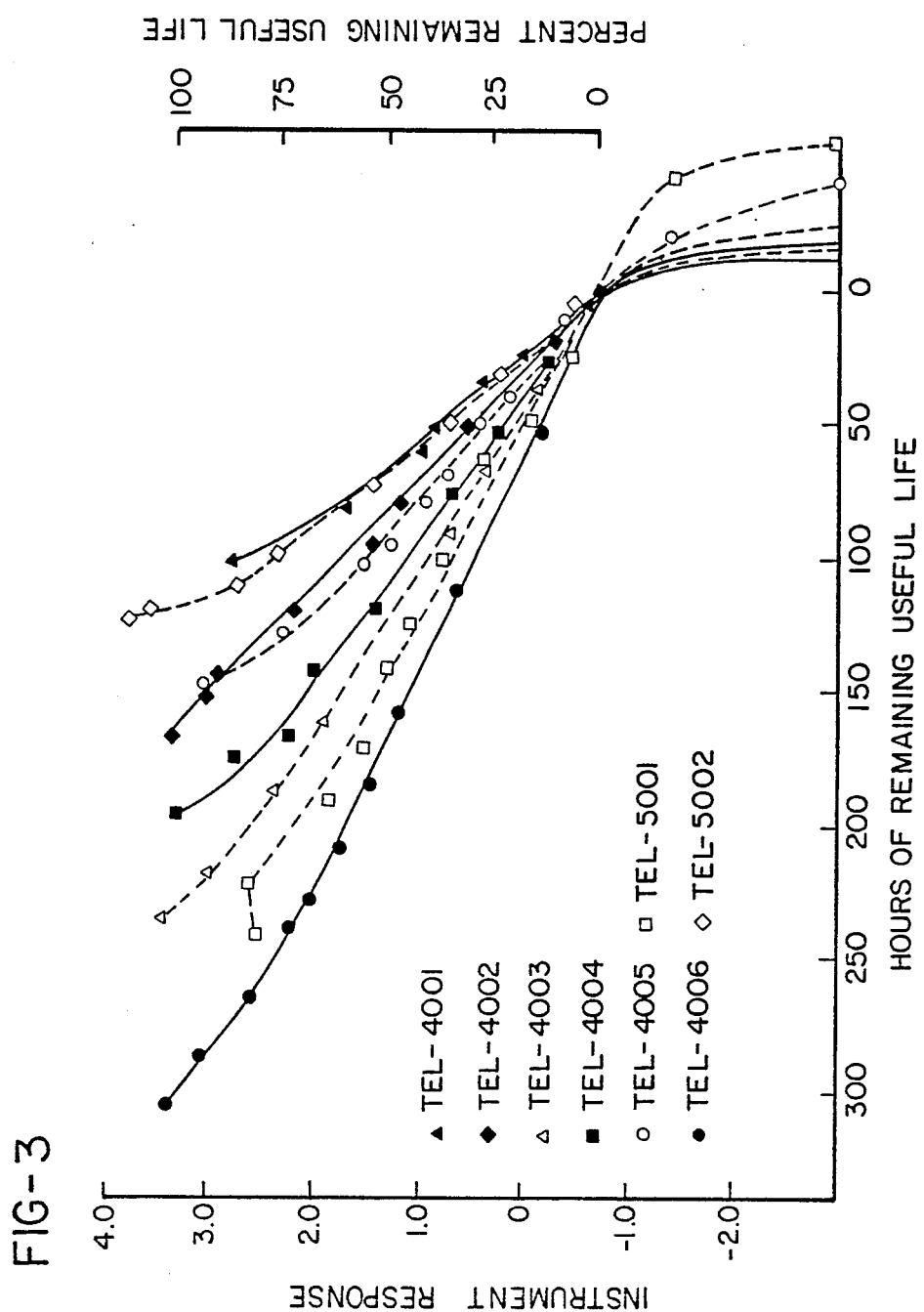
FIG. 3 is a plot illustrating typical results produced by the evaluation method.

The natural logarithm of the average reduction wave height for the sixth through tenth scans is plotted against the operating time of the equipment from which the sample was taken to produce the linear plots shown in FIG. 3. The data shown represents eight commercially-available gas turbine oil formulations, and each is an ester-based oil. The useful life for each oil formulation was devised by stressing the oil samples at 370° F. and plotting the physical properties of the stressed oil samples versus stressing time.

Since the plots of the multi-scan voltammetric results in FIG. 3 are linear and have the same value at the end of each oil's useful life, the percentage and hours of remaining useful life for each lubricant can be calculated using the following equations:

$$R_\% = \frac{\ln(H \text{ of sample}) - \ln(H \text{ of } 0\% \text{ standard})}{\ln(H \text{ of } 100\% \text{ standard}) - \ln(H \text{ of } 0\% \text{ standard})}$$

$$DR = \frac{\ln(H \text{ of sample 1}) - \ln(H \text{ of sample 2})}{T_2 - T_1}$$

$$R_H = \frac{\ln(H \text{ of sample}) - \ln(H \text{ of } 0\% \text{ standard})}{DR}$$

where $R_\%$ is the percentage of useful life remaining, H is the average reduction wave height of the sixth through tenth cyclic scans, 0% standard is an oil sample taken after the end of the lubricant's useful life, 100% standard is an oil sample of fresh lubricant, DR is the lubricant's depletion rate, T is the equipment operating time at which the sample was obtained, and $R_H$ is the hours of useful life remaining.

The results shown graphically in FIG. 3 demonstrate that the ester-oil evaluation technique is capable of accurately predicting an oil sample's percentage or hours of remaining useful life. Consequently, the correct oil change intervals for operating equipment, e. g., gas turbine-powered aircraft engines, can be predicted regardless of the oil formulation or specific operating conditions.

Figure 4:
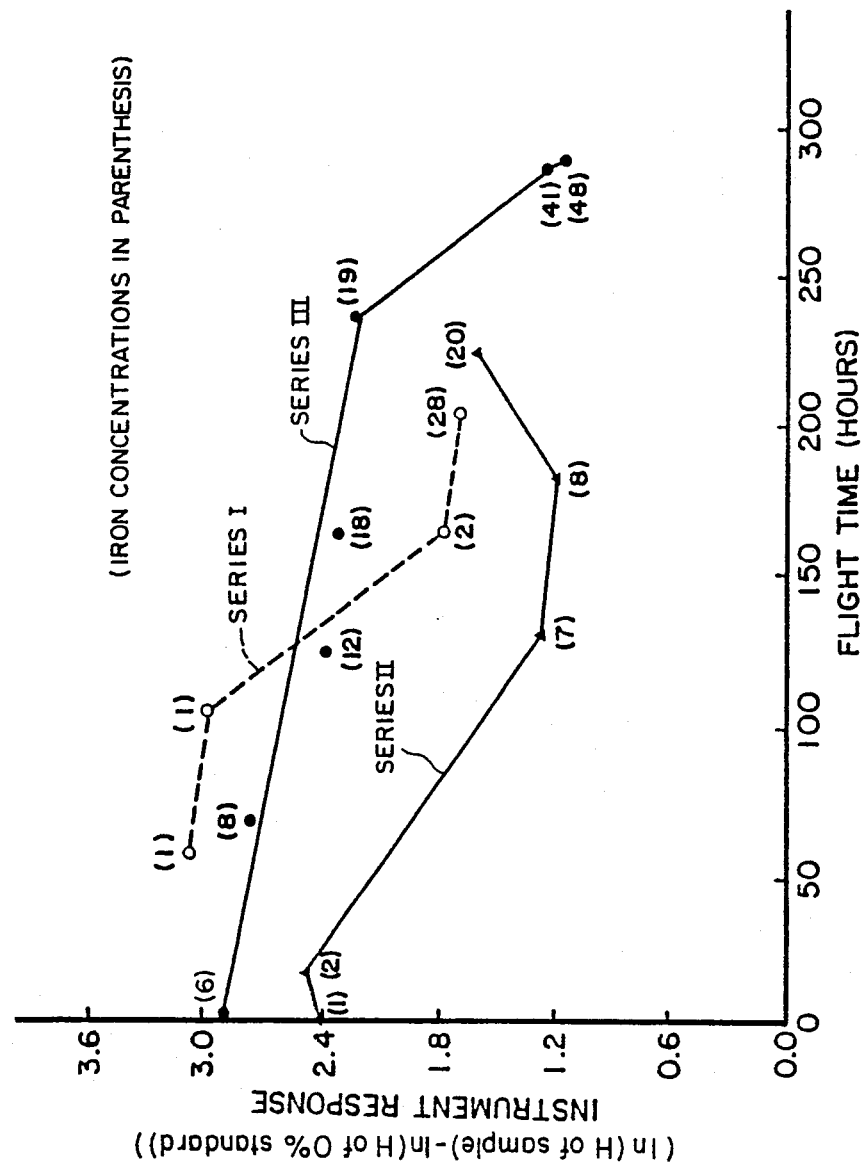
FIG. 4 is a plot illustrating evaluations performed on several gas turbine aircraft engines.

To further demonstrate the capabilities of the ester-oil evaluation technique, used oil samples of oil-type MIL-L-23699 were obtained from aircraft engines prior to engine failure. The remaining useful life evaluation method herein was performed on each of the samples obtained, as was a spectrometric oil analysis program currently in use. This latter technique provided iron concentrations within the oil samples expressed as parts per million. As seen by reference to FIG. 4, the oil sample series I and II include iron concentrations determined by the spectrometric oil analysis of less than ten parts per million prior to engine failure. (The final sample in each of these series was taken after engine failure.) However, in contrast to the iron concentrations, the method described herein provides responses which undergo dramatic decreases for the oil samples taken prior to engine failure. (The increase in the response prior to engine failure for the sample series II is the result of an oil dilution caused by introduction of fresh lubricant.) For the oil sample series III, both techniques provide results which undergo dramatic changes prior to engine failure.

While the method herein described constitutes a preferred embodiment of this invention, it is to be understood that the invention is not limited to this precise method, and that changes may be made therein without departing from the scope of the invention, which is defined in the appended claims.

What is claimed is:

1. A method for measuring the remaining useful life of a lubricant containing at least one antioxidant species, comprising the steps of:

mixing a lubricant sample with a solvent, organic base, and an electrolyte to produce an analysis sample;

placing said analysis sample into an electrolytic cell;

applying an electric potential of a first value to said analysis sample to produce an electric current therethrough;

varying said potential from said first value to a second value to produce an oxidation reaction of said antioxidant species within said cell;

varying said potential from said second value to said first value to produce a reduction reaction of an oxidized product of said antioxidant species within said cell; and measuring and recording said current during at least said reduction reaction.

2. The method as defined in claim 1, wherein said lubricant is an ester-based oil.

3. The method as defined in claim 1, wherein said organic base is pyridazine.

4. The method as defined in claim 1, wherein said organic base is pyridine.

5. The method as defined in claim 1, wherein said organic base is dipyridyl.

6. The method as defined in claim 1, wherein the ratio by weight of said organic base to said electrolyte and said solvent within said analysis sample is within the range of 1:300 to 1:30,000.

7. The method as defined in claim 6, wherein said ratio of said organic base to said electrolyte and said solvent is 1:3000.

8. The method as defined in claim 1, wherein the ratio by volume of said lubricant to said organic base, said electrolyte and said solvent within said analysis sample is within the range of 1:5 to 1:500.

9. The method as defined in claim 8, wherein said ratio of said lubricant to said organic base, said electrolyte and said solvent is 1:50.

10. The method as defined in claim 1, wherein said solvent is acetone.

11. The method as defined in claim 1, wherein said electrolyte is lithium perchlorate ($LiClO_4$).

12. The method as defined in claim 1, wherein said electrolytic cell includes a microelectrode, a reference electrode, and an auxiliary electrode.

13. The method as defined in claim 12, wherein said microelectrode is a glassy carbon electrode.

14. The method as defined in claim 12, wherein said reference electrode is Ag/AgCl.

15. The method as defined in claim 12, wherein said auxiliary electrode is a platinum wire.

16. The method as defined in claim 1, wherein said first and second potential values are within the range of +1.5 V and −1.5 V.

17. The method as defined in claim 16, wherein said first and second potential values are, respectively, 0.0 V and +1.0 V.

18. The method as defined in claim 17, wherein said potential is varied at a rate within the range of 0.2 V/sec to 30.0 V/sec.

19. The method as defined in claim 17, wherein said potential is varied at a rate of 5.0 V/sec.

20. The method as defined in claim 1, comprising the further step of determining the maximum current produced during said reduction reaction.

21. The method as defined in claim 1, comprising the further steps of:
repeating varying of said potential from said first value to said second value and to said first value for a plurality of times; and
continuing to measure and record said current during at least said reduction reactions produced during said varying.

22. The method as defined in claim 21, wherein varying of said potential from said first value to said second value and to said first value is performed ten times.

23. The method as defined in claim 22, comprising the further step of determining the maximum current produced during each of the sixth through tenth of said reduction reactions, and calculating therefrom an average maximum current value.

24. A method for measuring the remaining useful life of an ester-based lubricant containing at least one antioxidant species, comprising the steps of:
mixing a lubricant sample with a solvent, an organic base and an electrolyte to produce an analysis sample;
placing said analysis sample into an electrolytic cell;
subjecting said analysis sample to a cyclic voltammetric analysis comprising a plurality of cycles, whereby a varying electric current is produced within said cell; and
measuring and recording said current during said cyclic voltammetric analysis.

25. The method as defined in claim 24, comprising the further step of determining a maximum current value during a reduction reaction portion of said cyclic voltammetric analysis.

26. The method as defined in claim 24, comprising the further steps of determining a maximum current value during a reduction reaction portion of each of said cycles of said cyclic voltammetric analysis, and calculating from at least some of said maximum current values an average maximum current value.

27. The method as defined in claim 24, wherein said cyclic voltammetric analysis includes ten cycles.

* * * * *